United States Patent [19]

Gatto

[11] Patent Number: 5,068,388
[45] Date of Patent: Nov. 26, 1991

[54] BICYCLICTRIARYLPHOSPHITE ANTIOXIDANT

[75] Inventor: Vincent J. Gatto, Baton Rouge, La.

[73] Assignee: Ethyl Corporation, Richmond, Va.

[21] Appl. No.: 532,882

[22] Filed: Jun. 4, 1990

[51] Int. Cl.$^5$ ............................................. C07F 9/6574
[52] U.S. Cl. .................................................... 558/74
[58] Field of Search ..................................... 558/85, 74

[56] References Cited

U.S. PATENT DOCUMENTS 4,381,359  4/1983  Idel et al. ................................ 558/85
4,929,654  5/1990  Wang et al. ............................. 558/85

*Primary Examiner*—Mary C. Lee
*Assistant Examiner*—Michael G. Ambrose
*Attorney, Agent, or Firm*—Edgar E. Spielman, Jr.; Patricia J. Hogan

[57] ABSTRACT

Novel bicyclictriarylphosphite antioxidants are useful in protecting, against oxidation, materials normally susceptible to oxidation.

7 Claims, No Drawings

BICYCLICTRIARYLPHOSPHITE ANTIOXIDANT

BACKGROUND OF THE INVENTION

This invention relates to novel bicyclictriarylphosphites, processes for their manufacture, and their use in thermoplastic and thermoset formulations.

Tris(2,4-di-tert-butylphenyl)phosphite, a commercial antioxidant, exhibits relative ineffectiveness as a process stabilizer and color suppressant in polyolefin-based formulations In part, the ineffectiveness of this phosphite is due to its lack of good thermal and/or hydrolytic stability under polyolefin processing conditions. Under these conditions, this phosphite has a tendency to molecularly fragment, thereby yielding molecular fragments having a lower molecular weight than the original molecule. These molecular fragments are generally more volatile than the original molecule and thus can be lost from the formulation during processing. With these losses, the final product made from the formulation is deficient in the antioxidant loading needed. The molecular fragmentation is illustrated by the following scheme shown for hydrolytic fragmentation,

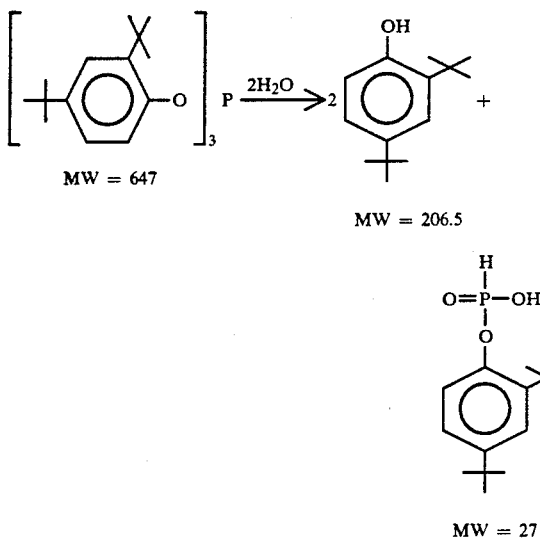

THE INVENTION

This invention provides for bicyclictriarylphosphite antioxidants which are thermally and hydrolytically stable under polyolefin processing conditions. Further, the antioxidants of this invention have a melting point which is compatible with their use in polyolefins.

The antioxidants of this invention can be generally represented by the structure,

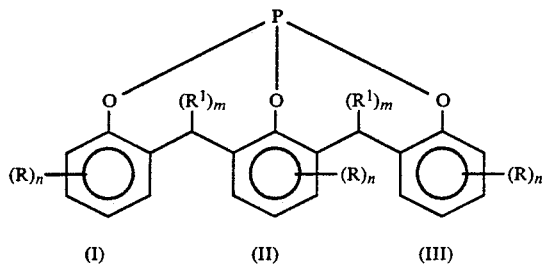

wherein, each R and $R^1$ is an independently selected $C_1$-$C_6$ alkyl radical, n = 1, 2 or 3 and m = 0 or 1. Preferred antioxidants are those in which any one or any combination of the following exists: m = 0; for each of the (I) and (III) aryl constituents, n = 2 and one R is a methyl radical and the other R is a tert-butyl radical; and, for the (II) aryl constituent, n = 1 and R is a methyl radical. Most preferred are,

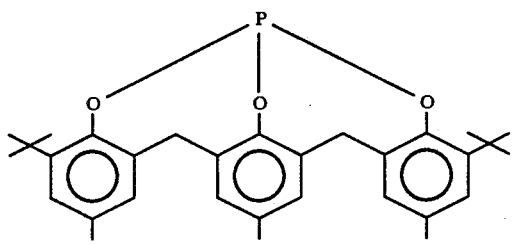

i.e., the phosphite of $\alpha^2,\alpha^6$-bis(3-tert-butyl-5methyl-2-hydroxyphenyl)mesitol, and

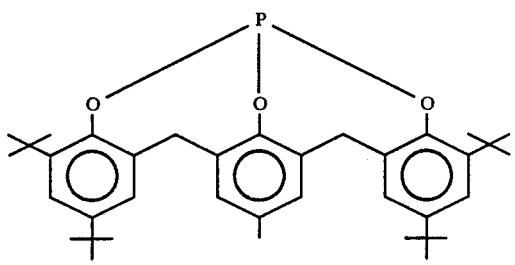

i.e., the phosphite of $\alpha^2,\alpha^6$-bis(3,5-di-tert-butyl-2-hyroxyphenyl)mesitol.

Exemplary of other useful bicyclictriarylphosphites are:

the phosphite of $\alpha^2,\alpha^6$-bis(3,5-dimethyl-2-hydroxyphenyl)-mesitol

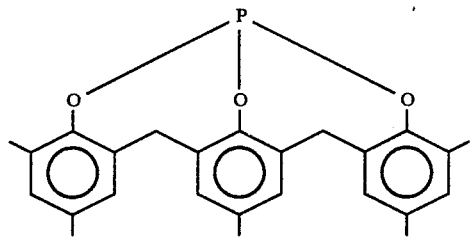

the phosphite of $\alpha^2,\alpha^6$-bis(3,5-di-tert-butyl-2-hydroxyphenyl)-$\alpha^2,\alpha^6$-dimethylmesitol

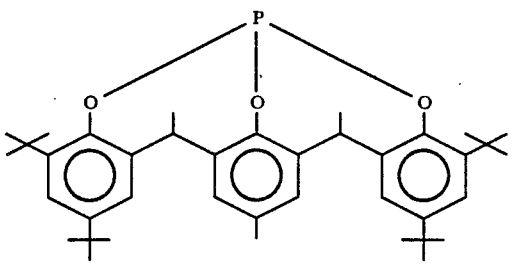

the phosphite of $\alpha^2,\alpha^6$-bis(3-tert-butyl-5-methyl-2-hydroxyphenyl)-$\alpha^2,\alpha^6$-dimethylme sitol

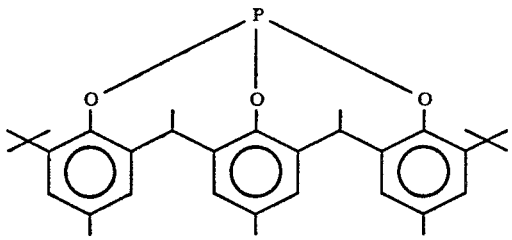

The bicyclictriarylphosphites of this invention are especially useful in formulation with both homopolymers and copolymers of blefinically unsaturated monomers. Exemplary of such polymers are: high density, medium density and low density polyethylene, ethylene-1-olefin copolymers, e.g., both block and random ethylene-propylene copolymers and ethylene-butylene copolymers; polypropylene; polybutylene; poly(4-methyl-1-pentane), etc.

Also the antioxidants of this invention may find utility in use with other organic materials such as: polyhalohydrocarbons, e.g., polyvinyl chloride; natural and synthetic rubbers, e.g., styrene-butadiene rubber, ethylene-propylenebutadiene terpolymers, polybutadiene, acrylonitrile-butadienestyrene resins; nitrogen-containing polymers, e.g., polyurethane; polyesters, e.g., polyethylene terephthalate; polystyrenic polymers; polyphenylene ethers; adhesive compositions; polyamides; petroleum oils; synthetic lubricants; and naturally occurring organic materials, such as grains, cellulose, etc.

The amount of bicyclictriarylphosphite used is generally small, say from about 0.005 to about 5 weight percent of the organic material to be protected against oxidation. Generally, a preferred range is from about 0.01 to about 2 weight percent.

Methods of incorporating the antioxidants into the organic material to yield a stabilized formulation are well known. For example, if the material is liquid, the antioxidant can be mixed into the material. Solid organic materials can be merely sprayed with a solution of the antioxidant in a volatile solvent, e.g., toluene. In the case of some polymers, the antioxidant can be added following the polymerization stage by mixing it with the final emulsion or solution polymerization mixture and then coagulating or removing the solvent to recover the stabilized polymer. It can also be added at the compounding stage by mixing the antioxidant with the rubbery polymer in commercial mixing equipment, such as a Banbury blender. In this manner, rubbery polymers, such as styrene-butadiene rubber, cispolybutadiene or isoprene polymers, are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

The antioxidants of the present invention can be used alone or can be used in combination with certain other phenolic antioxidants; thioesters, such as dilauryl thiodipropionate and distearyl thiodipropionate; UV light stabilizers, such as hindered amines or ultraviolet light absorbers; metal deactivators; pigments; dyes; lubricants, such as calcium stearate; nucleating agents; and talc and other fillers.

Exemplary phenolic antioxidants are 2,6-di-tert-butyl4-methylphenol; 2,6-di-tert-butyl-4-methoxymethylphenol; 2,6-dioctadecyl-4-methylphenol; 3,5-di-tert-butyl-4-hydroxyanisole; 2,5-di-tert-butyl-4-hydroxyanisole; 4-(hydroxymethyl)-2,6-ditert-butylphenol; 4,4'-methylenebis(2,6-di-tert-butylphenol); 2,2'-ethylidene-bis(4,6-di-tert-butylphenol); 4,4'-thiobis(2-methyl-6-tert-butylphenol); pentaerythrityltetrakis(3-(3',5'-di-tert-butyl-4'-hydroxyphenyl)propionate); 1,3,5-tris(3,5-ditert-butyl-4-hydroxybenzyl)isocyanurate; O,O'-di-n-octadecyl(3,5-di-tert-butyl-4-hydroxybenzyl)phosphonate; octadecyl 3-(3,5-di-tert-butyl-4-hydroxyphenyl)-propionate; 2,2'-oxamidobisethyl 3-(3,5-di-tert-butyl-4-hydroxyphenyl)propionate; calcium bis(O-ethyl(3,5-di-tert-butyl-4-hydroxybenzyl)phosphonate) and mixtures thereof. A particularly preferred phenolic antioxidant is 1,3,5-trimethyl-2,4,6-tris(3,5-di-tert-butyl-4-hydroxybenzyl)benzene which is available from Ethyl Corporation as ETHANOX ® 330 Antioxidant.

When utilized, the above phenolic antioxidants are preferably present with the antioxidant of this invention in an amount which is in the range of from about 0.005 to about 5 percent by weight based on the weight of the total formulation.

Some representative examples of useful UV stabilizers are:

UV Stabilizers

Nickel dibutyldithiocarbamate
2-hydroxy-4-n-octyloxybenzophenone
2,4-di-tert-butylphenyl 3,5-di-tert-butyl-4-hydroxybenzoate
Nickel bis[O-ethyl(3,5-di-tert-butyl-4-hydroxybenzyl) phosphonate
2-(3',5'-di-tert-butyl-2'-hydroxyphenyl)-5-chlorobenzotriazole
Bis(2,2,6,6-tetramethyl-4-piperidinyl)sebacate
Bis(1,2,2,6,6-pentamethyl-4-piperidinyl)sebacate
n-Butyl-(3,5-di-tert-butyl-4-hydroxybenzyl)-bis(1,2,2,6,6-pentamethyl-4-piperidinyl)malonate
Dimethyl succinate polymer with 2,2,6,6-tetramethyl-1-piperidine ethanol
N,N'-bis(2,2,6,6-tetramethyl-4-piperidinyl)-1,6-hexane diamine, polymer with 2,4,6-trichloro-1,3,5-triazine and 2,4,4-trimethyl-1,2-pentanamine
polymeric hindered amines such as Cyasorb ® UV3346 (American Cyanamid); Spinuvex ® A-36 (Montedison); Chimassorb ® 944 (Ciba-Geigy)
2-(2'-hydroxy-3',5'-di-tert-amylphenyl)benzotriazole
2,2'-thiobis(4-tert-octylphenolato)butylamino-Nickel-(II)
Nickel bis((ethyl-(3,5-di-tert-butyl-4-hydroxybenzyl)-phosphonate)
and the like.

Though the inventions disclosed herein are not to be bound by any particular theory, it is theorized that the antioxidants of this invention are not readily volatilized under polyolefin processing conditions because these antioxidants have a molecular configuration which will not readily fragment under such conditions to yield low weight molecular fragments. This is believed to be so even though some molecular bonds may be broken. Thus, the molecule remaining, though not necessarily the same as the initial molecule, has a weight comparable to the initial molecule and, as a result, will not tend to be volatilized from the polyolefin formulation to the same extent that smaller molecular fragments would. In support of this theory, for example, the following is believed to occur to the phosphite of $\alpha^2,\alpha^6$-bis(3,5-ditert-butyl-2-hydroxyphenyl)mesitol under hydrolytic conditions.

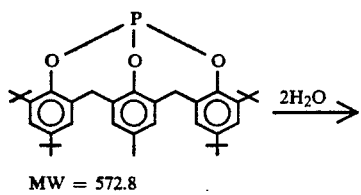

MW = 572.8

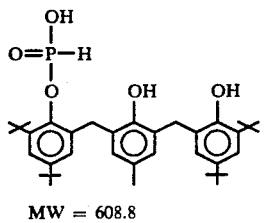

MW = 608.8

As can be seen the molecular weight of the surviving compound is not less than that of the original bicyclic-triarylphosphite despite the fracture of several molecular bonds. Thus, the surviving compound has a volatility approximately the same as that of the starting compound. Thermogravimetric analyses support this theory, see the Table infra.

The bicyclictriarylphosphites of this invention can be prepared by reacting the appropriate tris-phenol with a stoichiometric excess of PCl$_3$ in refluxing xylene and in the presence of a pyridine catalyst. The product can be purified by recrystallization using a methylene chloride/2-propanol system. The trisphenol reactant can be prepared by reacting the appropriate hindered phenol with a dialkylolalkylphenol. The reaction scheme is illustrated by the reaction sequence,

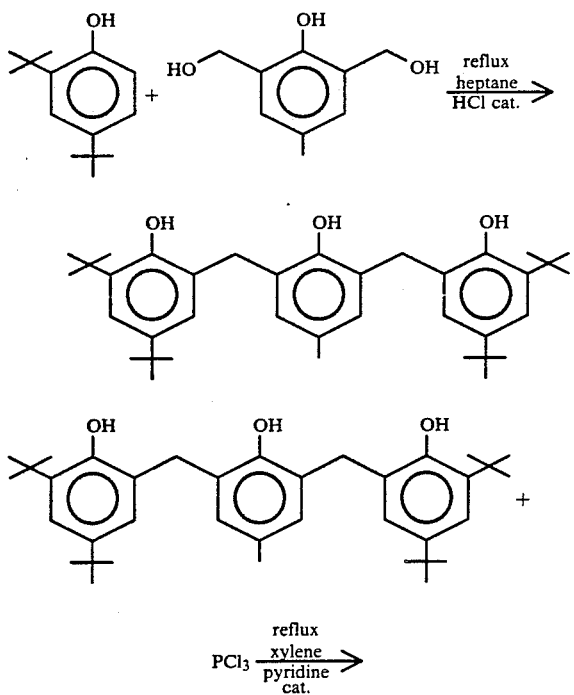

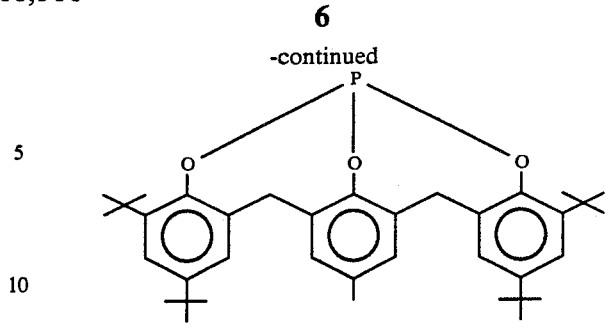

To produce the phosphite of $\alpha^2,\alpha^6$-bis(3-tert-butyl-5-methyl2-hydroxyphenyl)mesitol, the same reaction scheme is used except that the hindered phenol starting material is 2-tert-butyl-4-methylphenol.

The following Examples are illustrative of the features of this invention and are not to be taken as limiting.

EXAMPLE I

Preparation of the phosphite of $\alpha^2,\alpha^6$-bis(3-tert-butyl-5-methyl-2-hydroxyphenyl)-mesitol 2,6-Dimethylol-4-methylphenol (16.8 g, 0.10 mol), Aldrich, 97%) was added to a vigorously stirred solution of 2-tert-butyl-4-methylphenol (98.4 g, 0.60 mol, Aldrich, 99%) in heptane (50 mL). The resulting slurry was heated to dissolve the solids, cooled to 80° C., and then concentrated HCl (4 mL) was added. After the acid addition, the reaction was heated at reflux temperature for 4 hours while the water formed in the reaction was gradually removed via a Dean Stark Trap. The reaction was concentrated in vacuo and the excess 2-tert-butyl-4-methylphenol was separated from the product by bulb to bulb distillation using a Kugelrohr apparatus. The crude product was combined with heptane (100 mL), stirred at reflux for one hour, cooled to room temperature, and the solids isolated by filtration. This gave 28.4 g (61.6%) of product which was further purified by recrystallization from heptane (100 mL)/toluene (25 mL). This gave 20.9 g (45.3%) of $\alpha^2,\alpha^6$-bis(3-tert-butyl-5-methyl-2-hydroxyphenyl)mesitol as a white powder (mp 161-164° C.). H-NMR (C$_6$D$_6$) $\delta$1.37 (s, 18 H, tBu), 1 97 (s, 3 H, CH$_3$), 2.12 (s, 6 H, CH$_3$), 3.74 (s, 4 H, CH$_2$), 6.3 (broad s, 2 H, OH), 6.83 (s, 2 H, Ar), 6.89 (d, 2 H, Ar), 6.99 (d, 2 H, Ar), 7.5 (broad s, 1 H, OH). Gas Chromatography (G.C.) area percent analysis showed the product to be 94% pure.

The gas chromatography analysis was performed on a Hewlett Packard 5890A Gas Chromatograph equipped with FID detector and a 5 m HP-1 capillary column. The following temperature program was used: initial temperature 80° C., initial time 0, rate 8° C./min., final temperature 200° C., final time 0, rate A 10° C./min., final temperature A 280° C., final time A 7 minutes.

A solution containing the $\alpha^2,\alpha^6$-bis(3-tert-butyl-5-methyl-2-hydroxyphenyl)mesitol (18.4 g, 40 mmol), PCl$_3$ (7.0 g, 50 mmol, Aldrich, 98%), pyridine (1.6 g, 20 mmol, EM Reagent), and dry xylenes (50 mL), was stirred at reflux temperature for 6 hours. The reaction was cooled, filtered to remove pyridine.HCl, and the organic phase washed consecutively with saturated NaHCO$_3$ (100 mL), H$_2$O (2×100 mL), and finally saturated NaCl (100 mL). The organic phase was dried (MgSO$_4$) and concentrated in vacuo. This gave 16.5 g of crude product which was dissolved in methylene chloride (33 mL) and poured into hot and stirred 2-propanol (66 mL). The resulting slurry was slowly heated to 70° C. as methylene chloride was removed. At 70° C. the slurry was cooled to 5° C. and the precipitated solids were isolated by filtration. This gave 7.2 g (37%) of the phosphite of $\alpha^2,\alpha^6$-bis(3-tert-butyl-5-methyl2-hydroxyphenyl)mesitol as a white crystalline solid (DSC mp 204.6–207.1° C.). H-NMR (C$_6$D$_6$)$\delta$1.54 (s, 18 H, tBu), 1.99 (s, 3 H, CH$_3$), 2.18 (s, 6 H, CH$_3$), 3.59 (d, 2 H, CH$_2$), 4.41 (d, 2 H, CH$_2$), 6.76 (s, 2 H, Ar), 6.80 (d, 2 H, Ar), 7.14 (s, 2 H, Ar); $^{31}$P-NMR (C$_6$D$_6$) $\delta$123.0 (s); IR (C$_6$D$_6$) 3000, 2960, 2920, 2870, 1480, 1460, 1440, 1220, 1200, 1120, 920, 840, 820cm$^{-1}$; (M+) m/e calculated for C$_{31}$H$_{37}$O$_3$P =488. Found 488.

EXAMPLE II

Preparation of the phosphite of $\alpha^2,\alpha^6$-bis(3,5-di-tert-butyl-2-hydroxyphenyl)mesitol 2,6-Dimethylol-4-methylphenol (16.2 g, 0.093 mol, Aldrich, 97%) was added to a vigorously stirred solution of 2,4-di-tert-butylphenol (115.6 g, 0.56 mol, sample 65.85) in heptane (50 mL). The resulting slurry was heated to dissolve the solids, cooled to 80° C., and then concentrated HCl (4 mL) was added. After the acid addition the reaction was heated at reflux temperature for 4 hours while the water formed in the reaction was gradually removed via a Dean Stark Trap. The reaction was concentrated in vacuo and the excess 2,4-di-tert-butylphenol was separated from the product by bulb to bulb distillation using a Kugelrohr apparatus. The crude product was combined with heptane (100 mL), stirred at reflux for one hour, cooled to room temperature, and the solids isolated by filtration. This gave 30.6 g (60.4%) of product which was further purified by recrystallization from heptane (100 mL)/toluene (22.5 mL). This gave 18.1 g (35.7%) of $\alpha^2,\alpha^6$-bis(3,5-di-tert-butyl-2-hydroxyphenyl)mesitol as a white powder.

A solution containing the $\alpha^2,\alpha^6$-bis(3,5-di-tert-butyl-2-hydroxyphenyl)mesitol (18.0 g, 33 mmol, sample 7121-35-B), PCl$_3$ (5.7 g, 41 mmol, Aldrich, 98%), pyridine (1.3 g, 16.5 mmol, EM Reagent), and dry xylenes (50 mL), was stirred at reflux temperature of 6 hours. The reaction was cooled, filtered to remove pyridine.HCl, and the organic phase washed consecutively with saturated NaHCO$_3$ (100 mL), H$_2$O (2 ×100 mL), and finally saturated NaCl (100 mL). The organic phase was dried (MgSO$_4$) and concentrated in vacuo. This gave 20.5 g of crude product which was dissolved in methylene chloride (40 mL) and poured into hot and stirred 2-propanol (80 mL). The resulting slurry was slowly heated to 70° C. as methylene chloride was removed. At 70° C. the slurry was cooled to 5° C. and the precipitated solids were isolated by filtration. This gave 3.5 g (18.5%) of the phosphite of $\alpha^2,\alpha^6$-bis(3,5-di-tert-butyl-2-hydroxyphenyl)mesitol as a white crystalline solid (DSC mp 183.5–185.9° C.). H-NMR (C$_6$D$_6$) $\delta$1.33 (s, 18 H, tBu), 1.57 (s, 18 H, tBu), 1.99 (s, 3 H, CH$_3$), 3.64 (d, 2 H, CH$_2$), 4.49 (d, 2 H, CH$_2$), 6.73 (s, 2 H, Ar), 7.19 (d, 2 H, Ar), 7.49 (s, 2 H, Ar); $^{31}$P-NMR (C$_6$D$_6$) $\delta$123.6 (s); IR (C$_6$D$_6$) 2960, 2900, 2880, 1480, 1470, 1440, 1360, 1220, 1200, 120, 850cm$^{-1}$; (M+) m/e calculated for C$_{37}$H$_{49}$O$_3$P =572. Found 572.

The following Table illustrates the good thermal stability of the phosphites of this invention as compared to the commercial antioxidant, tris(2,4-di-tert-butylphenyl)phosphite.

TABLE

| Wt % loss | Thermogravimetric Analysis* | | |
|---|---|---|---|
| | Phosphite A °C. | Phosphite B °C. | Irgaphos ® 168 °C. |
| 10 | 327 | 313 | 275 |
| 50 | 372 | 358 | 320 |
| 90 | 393 | 376 | 339 |

Phosphite A Phosphite of $\alpha^2,\alpha^6$-bis(3-tert-butyl-5-methyl-2-hydroxyphenyl)mesitol
Phosphite B Phosphite of $\alpha^2,\alpha^6$-bis(3,5-di-tert-butyl-2-hydroxyphenyl)mesitol
Irgaphos ® 168 Tris(2,4-di-tert-butylphenyl)phosphite (a product sold by Ciba-Geigy).
*Theromogravimetric Analysis curves were run from 25° C. to 550° C. at 10 C.°/min. under nitrogen.

What is claimed is:

1. A bicyclictriarylphosphite corresponding to the formula:

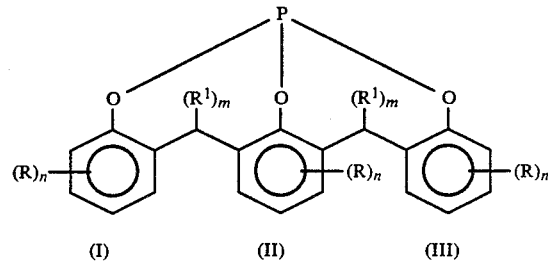

(I) (II) (III)

wherein R$^1$ is methyl, each R is independently selected from methyl and tert-butyl, m is 0 or 1, and n is an integer of 1–3.

2. The bicyclictriarylphosphite of claim 1 wherein, for each of the (I) and (III) aryl constituents, n=2 and one R is a methyl radical and the other R is a tert-butyl radical.

3. The bicyclictriarylphosphite of claim 1 wherein, for the (II) aryl constituent n=1 and R is methyl radical.

4. The bicyclictriarylphosphite of claim 1 wherein m=0.

5. The bicyclictriarylphosphite of claim 1 wherein m=1.

6. The bicyclictriaarylphosphite of claim 1 wherein the bicyclictriarylphosphite is the phosphite of $\alpha^2,\alpha^6$-bis(3-tert-butyl-5-methyl-2-hydroxyphenyl)mesitol, depicted as

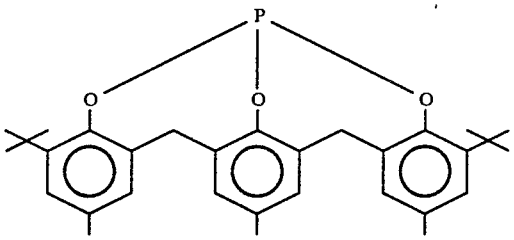

7. The bicyclictriarylphosphite of claim 1 wherein the bicyclictriarylphosphite is the phosphite of $\alpha^2,\alpha^6$-bis(3,5-di-tert-butyl-2-hydroxyphenyl)mesitol, depicted as

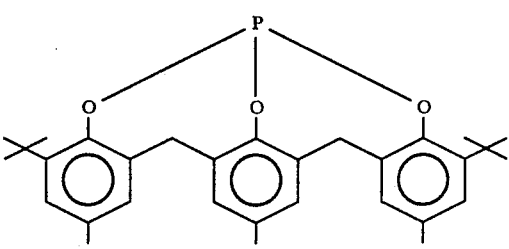

* * * * *

UNITED STATES PATENT AND TRADEMARK OFFICE
CERTIFICATE OF CORRECTION

PATENT NO. : 5,068,388

DATED : November 26, 1991

INVENTOR(S) : Vincent J. Gatto

It is certified that error appears in the above-identified patent and that said Letters Patent is hereby corrected as shown below:

Column 8, line 60, the formula reads:

"
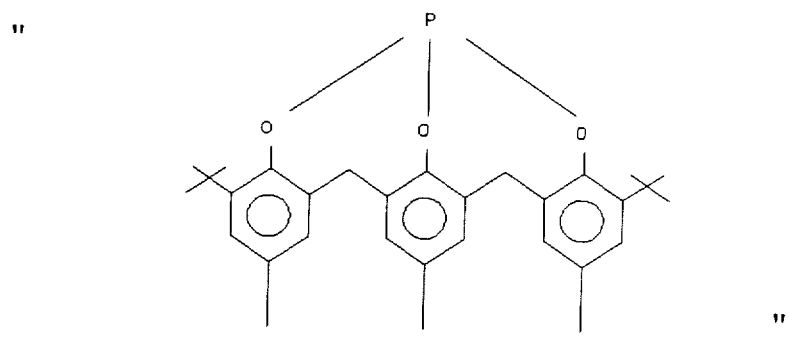
"

and should read

--
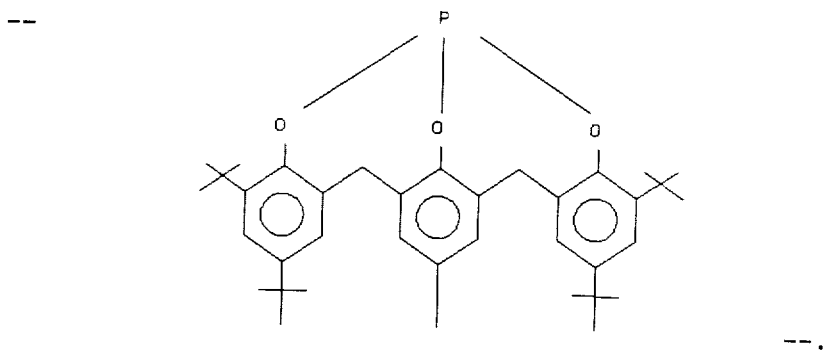
--.

Signed and Sealed this

Sixth Day of April, 1993

*Attest:*

STEPHEN G. KUNIN

*Attesting Officer*  *Acting Commissioner of Patents and Trademarks*